(12) United States Patent
Zou et al.

(10) Patent No.: US 9,324,549 B2
(45) Date of Patent: Apr. 26, 2016

(54) MEMS 2D AIR AMPLIFIER ION FOCUSING DEVICE AND MANUFACTURING METHOD THEREOF

(75) Inventors: Helin Zou, Liaoning (CN); Shuai Gao, Liaoning (CN)

(73) Assignee: DALIAN UNIVERSITY OF TECHNOLOGY, Ganjingzi Dalian, Liaoning (CN)

( * ) Notice: Subject to any disclaimer, the term of this patent is extended or adjusted under 35 U.S.C. 154(b) by 64 days.

(21) Appl. No.: 14/385,681

(22) PCT Filed: May 22, 2012

(86) PCT No.: PCT/CN2012/075903
§ 371 (c)(1),
(2), (4) Date: Sep. 16, 2014

(87) PCT Pub. No.: WO2013/163834
PCT Pub. Date: Nov. 7, 2013

(65) Prior Publication Data
US 2015/0060688 A1    Mar. 5, 2015

(30) Foreign Application Priority Data
Mar. 19, 2012    (CN) .......................... 2012 1 0073540

(51) Int. Cl.
| | |
|---|---|
| H01J 49/00 | (2006.01) |
| H01J 49/06 | (2006.01) |
| B81B 7/00 | (2006.01) |
| G01N 30/72 | (2006.01) |
| H01J 49/16 | (2006.01) |

(52) U.S. Cl.
CPC . *H01J 49/06* (2013.01); *B81B 7/00* (2013.01); *H01J 49/0018* (2013.01); *G01N 30/72* (2013.01); *H01J 49/165* (2013.01)

(58) Field of Classification Search
CPC ..... H01J 49/06; H01J 49/0018; H01J 49/165; B81B 7/00; G01N 30/72
USPC ...................... 250/396 R, 489, 428
See application file for complete search history.

(56) References Cited

U.S. PATENT DOCUMENTS 6,992,299 B2 *   1/2006   Lee ..................... H01J 49/10
                                              250/281
2003/0026740 A1   2/2003   Staats

FOREIGN PATENT DOCUMENTS

| CN | 1621945 A | 6/2005 |
|---|---|---|
| CN | 1811421 A | 8/2006 |
| GB | 2437844 A | 11/2007 |
| WO | WO 00/41214 A1 | 7/2000 |

* cited by examiner

*Primary Examiner* — Michael Maskell
(74) *Attorney, Agent, or Firm* — Muncy, Geissler, Olds & Lowe, P.C.

(57) ABSTRACT

The present invention relates to the field of micro electro mechanical system (MEMS), and particularly relates to a MEMS device of a two-dimensional (2D) air amplifier for electro spray ion focusing. It mainly includes original gas inlets, a gap structure, a wall structure and a center focusing groove in the axis of air amplifier. The feature of present invention is the double layers SU-8 mold fabricated by a micro machining method. Then the polydimethylsiloxane (PDMS) air amplifier is cast and bonded. In order to enhance the structure stiffness, PDMS is bonded with a glass supporting substrate. In the present invention, the fabrication method for the SU-8 mold and the PDMS casting and bonding processes are disclosed in detail so that the MEMS planar air amplifier ion focusing device can be fabricated by those skilled in the art. This fabrication method has advantages of simple process, low cost, small dimension size and easily implemented.

11 Claims, 2 Drawing Sheets

Figure 1:
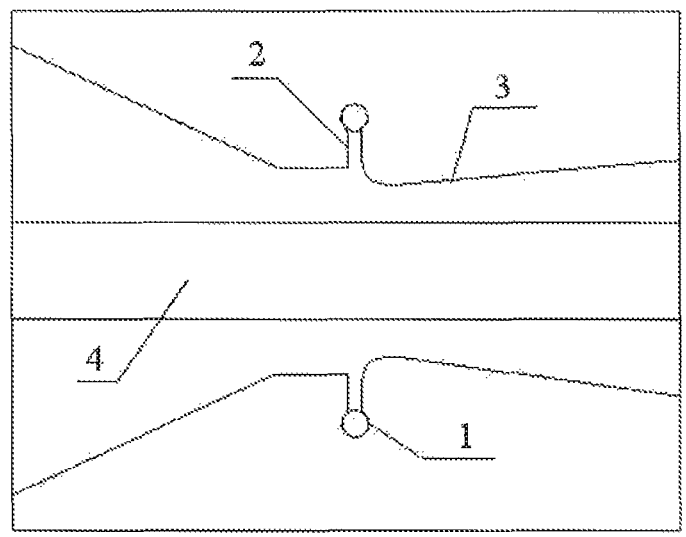

MEMS 2D AIR AMPLIFIER ION FOCUSING DEVICE AND MANUFACTURING METHOD THEREOF

FIELD OF THE INVENTION

The present invention relates to the field of microelectromechanical systems (MEMS) research, and particularly relates to a MEMS two-dimensional air amplifier device for electrospray ion focusing.

BACKGROUND OF THE INVENTION

In recent years, substantial amount of research work has been done in order to improve the sensitivity and resolution of the electro spray mass spectrometry (ESI-MS). The key technology is how to enhance the transmission efficiency of sampling ion generated by ESI and transferred into the mass spectrum more effectively. The air amplifier is an aerodynamics device, which focuses ions into the inlet of MS using Coanda effect and Venturi effect.

The working process of the air amplifier can be described as follows. The gas enters into the chamber from the inlet, and the gas was extruded in the gap and its velocity is increased. The gas moves along the wall by the Coanda effect and a pressure drop generated by the high speed gas velocity occurs due to the Venturi effect, which induces the airflow around the wall surface. The ion plume is focused and speeded up in the center area of the ion focusing groove. Therefore, the transmission efficiency is improved in this way.

People have studied the role of commercial air amplifier in electrospray mass spectrometry system, which can improve the quantity of ions. However, there are disadvantages of the commercial air amplifier such as the large size, complication structure and high cost. These disadvantages are not favorite for the miniaturization of the ESI-MS system and not suitable for the nano-ESI source.

DETAILED DESCRIPTION OF THE INVENTION

This invention offers a solution to the technical problems of the commercial air amplifier, such as the non-optimized large dimension structure, complicated structure and high cost. This invention provides a fabricated method for a MEMS 2D air amplifier ion focusing device with low cost and simple structure.

A MEMS 2D air amplifier ion focusing device is consist of a chamber structure and a glass substrate. There is an original gas inlet formed in the glass supporting substrate and the body chamber. There is a gap structure at the gas inlet of the chamber. The gas outlet connects with the wall structure. There is also a center area of the ion focusing groove in the axis of air amplifier.

The said original gas inlets are set in the both sides of axis of the said MEMS 2D air amplifier ion focusing device. It could have one or more original gas inlets per side with the same number of original gas inlets for both sides.

The said gap structure can be any angle with the axis of amplifier in the said MEMS 2D air amplifier ion focusing device The said wall surface structure can be consisted by a smooth plane or a curveded surface in the said MEMS 2D air amplifier ion focusing device.

The said gap structure and the wall surface structure can be connected by a transition curveded surface in the said MEMS 2D air amplifier ion focusing device.

The said structure of the center area of the ion focusing groove can be rectangle or any other shapes. Also, it is always set between amplifier's wall surfaces in the said MEMS 2D air amplifier ion focusing device The said glass substrate can be polymer, silicon or ceramic materials in the said MEMS 2D air amplifier ion focusing device The micromachining processing of the said MEMS 2D air amplifier ion focusing device is shown as follows:

(1) The fabrication of 2D air amplifier mold includes two photolithography steps:

The first photolithography: to oxidize a layer of silicon dioxide on silicon wafer. Then, spin coat a layer of photoresist with 150 μm thick followed by a prebake step. Make two mask plates. There is the wall pattern of amplifier and alignment mark in the first mask plate. The width of gap is 50 μm. There is the pattern of center area of the ion focusing groove and alignment marks. Put the first mask plate on the photoresist layer and expose it under the ultraviolet light. Then, postbake the photoresist layer to obtain the crosslink layer. The first layer mold with gaps, wall surface and alignment marks structure is completed after developing.

The second photolithography: spin coat the second photoresist layer with 350 μm thick and prebake the photoresist. Put the second mask onto the photoresist layer. Align the mark of the first photolithography with the one on the second mask plate. Then, expose it under the ultraviolet light. Then, postbake the photoresist layer to obtain the crosslink layer. The second layer mold with the microstructure of the center area of the ion focusing groove gaps, wall surface and alignment marks structure is completed after developing.

The mold of MEMS 2D air amplifier is fabricated by the above said two photolithography steps.

(2) The chips casting: after making the MEMS 2D amplifier mold, casting PDMS to obtain a PDMS amplifier structure. Casting another one in the same way.

(3) The first chips bonding: drill a hole near to the gap in one of the PDMS structure as a gas inlet. Bond two PDMS chips together by the aligning marks to obtain a whole PDMS air amplifier.

(4) The second chips bonding: drill a hole on the glass in the same position of the said whole PDMS air amplifier. Then, bond the glass with the PDMS air amplifier to form the final MEMS 2D air amplifier focusing device.

The said angle between gap and the axis of amplifier and the width of gap is adjustable by designing the first mask plate when fabricating the MEMS 2D air amplifier ion focusing device.

The said height of MEMS 2D amplifier mold is adjustable by spinning the photoresist with the different thickness when fabricating the MEMS 2D air amplifier ion focusing device.

The said PDMS amplifier structure can be formed in one time and bonded with the plate when fabricating the MEMS 2D air amplifier ion focusing device.

The gas enters into the chamber from the gap inlet, and the gas was extruded in the gap and its velocity is increased. The nitrogen gas moves along the right side of wall by the Coanda effect and a pressure drop generated by the high speed nitrogen gas velocity occurs due to the Venturi effect, which induces the airflow around the wall surface. The electrospray ions are focused and desolvated by the induced airflow. Therefore, the transmission efficiency is improved in this way. The present invention has the advantages of simple fabrication process, low cost and small dimension size.

CAPTIONS OF THE ATTACHED FIGURES

The following attached figures are the detailed description of this invention.

FIG. 1 The cross section profile of the first exemplary embodiment of MEMS 2D air amplifier ion focusing device.

Figure 2:
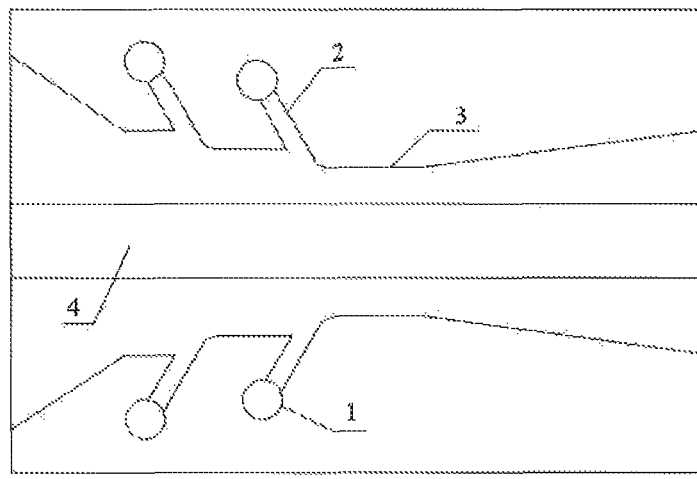

FIG. 2 The cross section profile of the second exemplary embodiment of MEMS 2D air amplifier ion focusing device in accordance with the first exemplary embodiment.

Figure 3:
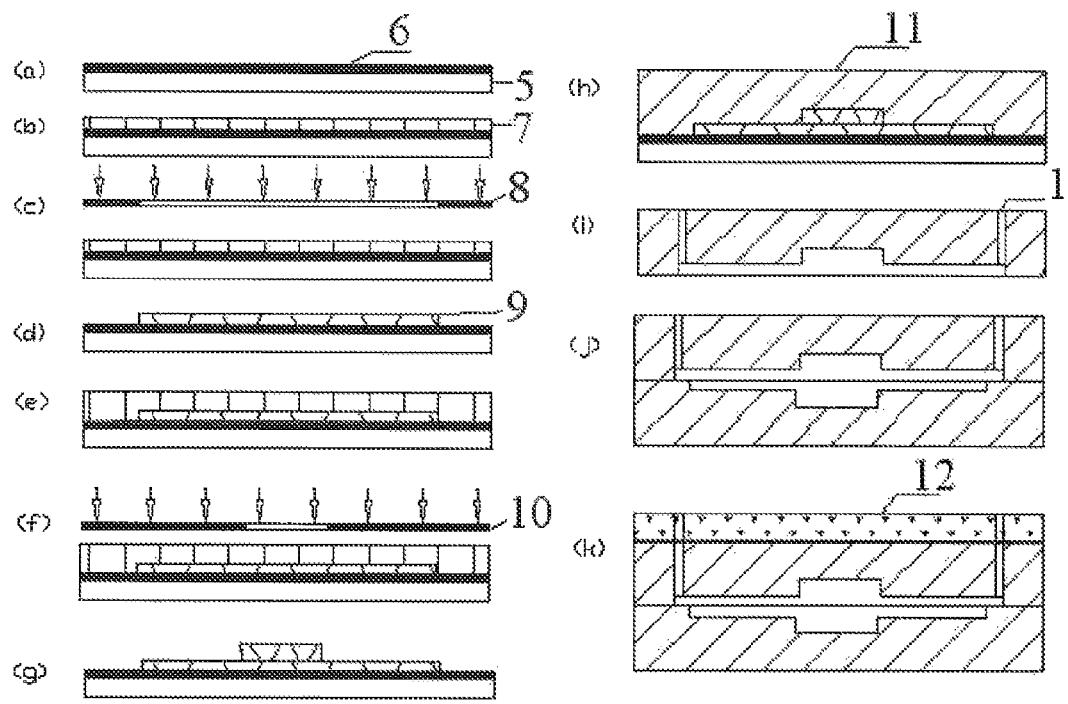

FIG. 3 The schematic of fabrication process of MEMS 2D air amplifier ion focusing device.

Figure 4:
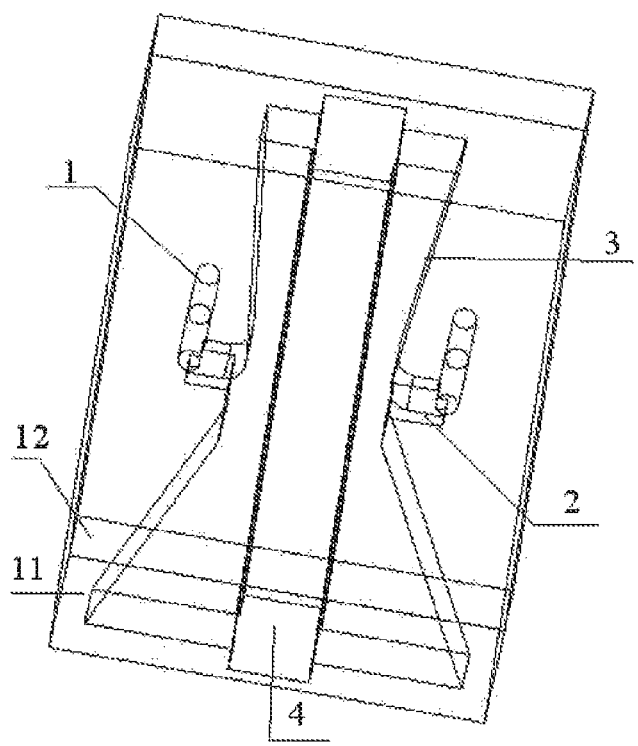

FIG. 4 The schematic structure of the first exemplary embodiment of MEMS 2D air amplifier ion focusing device.

In the figures: 1 inlet, 2 gap, 3 wall, 4 center area of the ion focusing groove, 5 silicon wafer, 6 silicon dioxide, 7 photoresist layer, 8 the first mask plate, 9 crosslink layer, 10 the second mask plate, 11 PDMS, 12 glass substrate.

DETAILED DESCRIPTION OF THE FABRICATION PROCESS

Referring to the FIG. 1 to FIG. 4, FIG. 1 illustrates the cross section profile of the first exemplary embodiment of MEMS 2D air amplifier ion focusing device. FIG. 2 is the cross section profile with some defined angle between the gap and the wall. FIG. 3 is the process flow of MEMS 2D air amplifier device ion focusing. FIG. 4 is the schematic structure of the first exemplary embodiment of MEMS 2D air amplifier ion focusing device.

As shown in FIG. 1, the more charged ions are expected to be able to enter into the mass spectrometer after the charged electrospray droplets were formed. This MEMS 2D air amplifier ion focusing device is invented in order to improve the sensitivity of the mass spectrometer. The present invention includes air amplifier chamber structure and a stiff supporting substrate. The original gas inlet (1) is designed in the glass supporting substrate of air amplifier and chamber. There is a gap structure (2) in the gas inlet of the air amplifier chamber. The wall structure is designed behind the gap's outlet. The center area of the ion focusing groove (4) is made symmetrically in the axis of air amplifier.

The nitrogen gas enters into the chamber from the inlet, and the nitrogen gas was extruded in the gap and its velocity is increased. The gas moves along the wall by the Coanda effect and a pressure drop generated by the high speed gas velocity occurs due to the Venturi effect, which induces the airflow around the wall surface. The ion plume is focused and speeded up in the center area of the ion focusing groove. Therefore, the transmission efficiency is improved in this way.

As shown in the FIG. 3(a), put the silicon wafer 5 into oxidation oven after cleaning with the standard cleaning liquid, which makes silicon covered by the silicon dioxide 6 as a substrate. As shown in the FIG. 3(b), spin a 2075 SU-8 layer 7 with a 150 μm thick onto the silicon dioxide layer 5 at the spin speed of 1400 rpm, spin duration of 30 seconds. As shown in the FIG. 3(c) two mask plates are used. The first one has an amplifier gap, wall pattern and alignment mark. The width of the gap is 50 μm. The second mask plate has a pattern of the center area of the ion focusing groove and alignment marks. Bake the said SU-8 photoresist layer at 85° C. for 3 hours and align the first mask plate 8 onto the SU-8 photoresist layer. The pattern of mask plate is transformed into the SU-8 photoresist layer after ultraviolet exposing. As shown in FIG. 3(d), post bake the exposed SU-8 photoresist layer at 85° C. for 3 minutes. After the developing, the first cross bonding layer 9 is obtained which includes the micro structure of the gap 2 and wall 3 and alignment marks. As shown in FIG. 3(e), spin a layer of 2075 SU-8 with a 350 μm thick on the first layer structure. The spin speed is 700 rpm. The spin time is 12 seconds. As shown in FIG. 3(f), prebake the photoresist for 5 hours. Then, align the second mask plate 10 onto the SU-8 photoresist layer. The pattern of mask plate is transformed into the SU-8 photoresist layer after ultraviolet exposing. As shown in FIG. 3(g), after 4 minutes post-baking at 85° C., the second layer of cross link layer can be formed by developing. Until now the mold of air amplifier is finished. As shown in FIG. 3(h), mix the curing agent and the prepolymer 11 of PDMS in 1:5. Then, put the mixture into the vacuum chamber for 30 minutes to get rid of the bubbles. Cast the mixture into MEMS 2D air amplifier mold and place it into the oven for 1 hour at 60° C. As shown in FIG. 3(i) Peal the partly solidified PDMS from the mold. Then a piece of air amplifier structure is got. As shown in FIG. 3(j), cast another air amplifier structure with the mixture of 1:20. Drill a hole 1 near the gap on the one of PDMS. Align the two PDMS under microscope. At last, put the aligned PDMS chips into the oven at 60° C. for 3 hours to obtain the permanent bonded PDMS chips. As shown in FIG. 3(k), firstly, drill a hole on the glass 12 by the ultrasonic drilling machine. The glass hole is placed in the same position with the one of the air amplifier. Secondly, clean the glass with concentrated sulfuric acid and hydrogen peroxide mixed in 5:1. Dry the glass with oven after cleaning. Lastly, bond PDMS amplifier with the glass substrate permanently with the oxygen plasma treatment. The structure strength is increased in this bonding method.

The summary of fabrication process flow for the structure of FIG. 1 is shown as follows (FIG. 3):

(a) Put the silicon wafer 5 into oxidation oven after cleaning with the standard cleaning liquid, which makes silicon covered by the silicon dioxide 6 as a substrate. As shown in the Figure (b) Spin a 2075 SU-8 layer 7 with a 15011 m thick on the silicon dioxide layer 5.

(c) Prebake the SU-8 photoresist layer and align the first mask plate 8 onto the SU-8 photoresist layer. The pattern of the mask plate is transformed into the SU-8 photoresist layer under ultraviolet exposing.

(d) Postbake the exposed SU-8 photoresist layer. After enveloping, the first cross bonding layer 9 is obtained which includes the micro structure of the gap 2 and wall 3 and alignment marks.

(e) Spin the second layer of 2075 SU-8 with a 350 μm thick on the first layer structure.

(f) Prebake the photoresist. Then, align the second mask plate 10 with the SU-8 photoresist layer. The pattern of mask plate is transformed into the SU-8 photoresist layer after ultraviolet exposing.

(g) Postbake the photoresist, the second layer of cross link layer can be formed by developing which includes the structure of center area of the ion focusing groove 4. Until now the mold of air amplifier is finished.

(h) Cast PDMS 11 by using MEMS 2D air amplifier mold.

(i) Peal the partly solidified PDMS off the mold. Then a piece of air amplifier structure is obtained.

(j) Cast another piece of air amplifier structure in the same way. Align and bond the two pieces of PDMS permanently under microscope.

(k) Finally, bond PDMS air amplifier with the glass substrate 12 permanently.

The final structure of MEMS 2D air amplifier ion focusing device fabricated by the above process flow is shown in FIG. 4.

The structure of air amplifier shown in FIG. 2 can also be fabricated by using the present invention in the same way as above description for the structure of FIG. 1. However there are some differences in step (c). The angle between the gap and the wall and the width of the gap are adjustable. The structure of MEMS 2D air amplifier ion focusing device in FIG. 2 can be fabricated by designing the first mask plate. The structure of MEMS 2D air amplifier mold with high aspect ration can be realized by adjusting the thickness of the photoresist spun. Then, cast the PDMS to form the PDMS air amplifier structure in one step. Bond the PDMS to form the MEMS 2D air amplifier ion focusing device. The alignment marks in present invention can be made by either dry etching or wet etching in the back side of the silicon wafer.

The above described methods are only the optimum ones of present invention, which cannot be the pattern limitation. All equivalent structures and process flows related to the attached figures in the present invention directly/indirectly applied in the other relevant technical areas are also included within the pattern protective area of the present invention.

The invention claimed is:

1. A MEMS 2D air amplifier ion focusing device includes air amplifier chamber structure and glass supporting substrate (12), the feature of this devise is that the original gas inlet (1) is designed in the said glass supporting substrate and the chamber of the air amplifier, there is a gap structure (2) in the original gas inlet of the air amplifier chamber, the wall structure (3) is designed at the gap's outlet, the center area of the ion focusing groove (4) is made symmetrically along the axis of air amplifier device.

2. According to the claim 1, the feature of the said MEMS 2D air amplifier ion focusing device is that the original gas inlet is disposed symmetrically on both sides of the amplifier's axis, the number of the original gas inlet on a single side of the 2D air amplifier device may be one or more than one, however both sides of the 2D air amplifier device should have equal number of the gas inlets.

3. According to the claim 1, the feature of the said MEMS 2D air amplifier ion focusing device is that the gap structure of the said original gas inlet can be at any angle with the axis of the air amplifier.

4. According to the claim 1, the feature of the said MEMS 2D air amplifier ion focusing device is that the said wall structure is consist of smooth flat and curved surface.

5. According to the claim 1, the feature of the said MEMS 2D air amplifier ion focusing device is the said gap structure and the said wall structure are mutually connected by a curved wall surface.

6. According to the claim 1, the feature of the said MEMS 2D air amplifier ion focusing device is that the said structure of the center area of the ion focusing groove is in the shape of rectangle, it is always set between the two side walls of the air amplifier.

7. According to the claim 1, the feature of the said MEMS 2D air amplifier ion focusing device is that the said glass supporting substrate can be made of polymer, silicon, ceramic or any other suitable material.

8. According to claim 1, the feature of any said MEMS 2D air amplifier ion focusing device includes the following fabrication process steps:

(1) the fabrication of 2D air amplifier mold structure comprises two photolithography steps:

the first photolithography: to oxidize a layer of silicon dioxide on silicon wafer, then, spin a layer of photoresist with 150 μm thick and prebake the photoresist, make two mask plates, there is the wall pattern of amplifier and alignment mark in the first mask plate, the width of gap is 50 μm, there is the pattern of center area of the ion focusing groove and alignment marks in the second mask plate, put the first mask plate on the photoresist layer and expose it under the ultraviolet light, then, postbake the photoresist layer to obtain the crosslink layer, the first layer mold with gaps, wall surface and alignment marks structure is completed after developing;

the second photolithography: spin the second photoresist layer with 350 μm thick and prebake the photoresist, put the second mask onto the photoresist layer, align the mark of the first photolithography with the one on the second mask plate, then, expose it under the ultraviolet light, then, postbake the photoresist layer to obtain the crosslink layer, the second layer mold with the microstructure of the center area of the ion focusing groove gaps, wall surface and alignment marks structure is completed after developing;

the mold of MEMS 2D air amplifier is fabricated by the above said two photolithography steps;

(2) The chips casting: after obtaining the MEMS 2D amplifier mold micro structure, cast PDMS to make a PDMS amplifier structure, cast another one in the same way;

(3) The first steps of the chip bonding: drill a hole near to the gap in one of the PDMS structure to form a gas inlet, bond two PDMS chips together by the aligning marks to obtain the PDMS air amplifier;

(4) The second step of the chip bonding: drill a hole on the glass in the same position of the said PDMS air amplifier, then, bond the glass with the PDMS air amplifier to form the final MEMS 2D air amplifier focusing device.

9. According to the claim 8, the feature of the said fabrication method of the MEMS 2D air amplifier ion focusing device is that the gap width and the gap angle with the amplifier axis can be adjustable by designing the first mask plate.

10. According to the claim 8, the feature of the said fabrication method of the MEMS 2D air amplifier ion focusing device is that the height of the said MEMS 2D air amplifier ion focusing device can be adjustable by changing the thickness of the spin-coated photoresist.

11. According to the claim 8, the feature of the said fabrication method of the MEMS 2D air amplifier ion focusing device is that the said PDMS air amplifier can be made in one time and then bond with the PDMS plate.

* * * * *